(12) United States Patent
Warntjes (10) Patent No.: US 10,888,246 B2
(45) Date of Patent: Jan. 12, 2021

(54) METHOD AND SYSTEM FOR GENERATING A CONTRAST ENHANCEMENT MAP

(71) Applicant: Synthetic MR AB, Linköping (SE)

(72) Inventor: Marcel Warntjes, Ljungsbro (SE)

(73) Assignee: Synthetic MR AB, Linkoeping (SE)

( * ) Notice: Subject to any disclaimer, the term of this patent is extended or adjusted under 35 U.S.C. 154(b) by 475 days.

(21) Appl. No.: 15/652,721

(22) Filed: Jul. 18, 2017

(65) Prior Publication Data
US 2019/0021624 A1    Jan. 24, 2019

(51) Int. Cl.
*A61B 5/055* (2006.01)
*A61B 5/042* (2006.01)
(Continued)

(52) U.S. Cl.
CPC ............ *A61B 5/055* (2013.01); *A61B 5/0042* (2013.01); *G01R 33/50* (2013.01); *G06T 7/0014* (2013.01);
(Continued)

(58) Field of Classification Search
CPC .............. G01R 33/56; G01R 33/5601; G01R 33/5602; G01R 33/5608; G01R 33/50;
(Continued)

(56) References Cited

U.S. PATENT DOCUMENTS 4,720,679 A * 1/1988 Patrick ................... G01R 33/24
                                                                            324/309
9,488,711 B2 * 11/2016 Kimura ................... A61B 5/489
(Continued)

OTHER PUBLICATIONS

Iglesias JE, Konukoglu E, Zikic D, Glocker B, Van Leemput K, Fischl B. Is synthesizing MRI contrast useful for inter-modality analysis? Med Image Comput Comput Assist Interv. 2013;16(Pt 1):631-638. doi:10.1007/978-3-642-40811-3_79 (Year: 2013).*

(Continued)

*Primary Examiner* — Bill Thomson
*Assistant Examiner* — Amy J Shafqat
(74) *Attorney, Agent, or Firm* — Oblon, McClelland, Maier & Neustadt, L.L.P.

(57) ABSTRACT

The present document relates to a method for generating a contrast enhancement map of a portion of a patient. The method comprises acquiring a magnetic resonance, MR, quantification sequence of the portion, wherein the MR quantification sequence comprises quantification information of a longitudinal R1 relaxation rate, R1, and proton density, PD, of the portion, generating an R1 map of the portion based on the MR quantification sequence, wherein a value of R1 for each voxel of the R1 map is determined, generating a PD map of the portion based on the MR quantification sequence, wherein a value of PD for each voxel of the PD map is determined, estimating a R1' map of the portion, based on the PD map and a predetermined relationship of R1 and PD of the portion, wherein an estimated value of R1 for each voxel of the R1' map is calculated, generating a delta R1 map based on the R1 map and the R1' map. The voxels of the R1 map, of the PD map, of the R1' map, and of the delta R1 map, have a one to one correspondence. A value of each voxel of the delta R1 map represents a difference of R1 values of the corresponding voxel of the R1 map and of the corresponding voxel of the R1' map.

35 Claims, 3 Drawing Sheets

(51) Int. Cl.
*G06T 7/00* (2017.01)
*A61B 5/00* (2006.01)
*G01R 33/50* (2006.01)
*G01R 33/56* (2006.01)

(52) U.S. Cl.
CPC ........... *A61B 5/6814* (2013.01); *A61B 5/6823* (2013.01); *A61B 5/6824* (2013.01); *A61B 5/6828* (2013.01); *A61B 2576/026* (2013.01); *G01R 33/5601* (2013.01); *G01R 33/5608* (2013.01); *G06T 2207/10088* (2013.01); *G06T 2207/30016* (2013.01); *G06T 2207/30096* (2013.01)

(58) Field of Classification Search
CPC ..... A61B 5/055; A61B 5/0042; A61B 5/6814; A61B 5/6824; A61B 5/6823; A61B 5/6828; A61B 2576/026; G06T 2207/30096; G06T 2207/30016; G06T 2207/10088; G06T 7/0014
See application file for complete search history.

(56) References Cited

U.S. PATENT DOCUMENTS

| | | | | |
|---|---|---|---|---|
| 10,194,829 B2* | 2/2019 | Kaditz | ................... | A61B 5/055 |
| 10,222,441 B2* | 3/2019 | Kaditz | ................... | G01R 33/48 |
| 10,330,757 B2* | 6/2019 | Katscher | ................ | G01R 33/54 |
| 10,401,444 B2* | 9/2019 | Taniguchi | .............. | G01R 33/50 |
| 10,571,543 B2* | 2/2020 | Ye | .................... | G01R 33/56545 |
| 10,698,060 B2* | 6/2020 | Shiodera | ................ | A61B 5/0555 |
| 2010/0103166 A1* | 4/2010 | Warntjes | ................ | A61B 5/055 345/419 |
| 2010/0253342 A1* | 10/2010 | Kimura | ................ | A61B 5/0275 324/309 |
| 2011/0018537 A1* | 1/2011 | Warntjes | ............ | G01R 33/5602 324/309 |
| 2014/0180061 A1* | 6/2014 | Warntjes | ................ | G01R 33/50 600/416 |
| 2015/0177350 A1* | 6/2015 | Warntjes | ................ | G01R 33/50 324/309 |

OTHER PUBLICATIONS

Bruno Alfano, et al. "Multiparametric Display of Spin-Echo Data from MR Studies of Brain", Journal of Magnetic Resonance Imaging, vol. 5, No. 2, 1995, pp. 217-225.

Maria Engström, et al. "Multi-Parametric Representation of Voxel-Based Quantitative Magnetic Resonance Imaging", PLoS ONE, vol. 9, No. 11, 2014, pp. 1-10.

Janne West, et al. "Application of Quantitative MRI for Brain Tissue Segmentation at 1.5 T and 3.0 T Field Strengths", PLoS ONE, vol. 8, No. 9, 2013, pp. 1-12.

* cited by examiner

METHOD AND SYSTEM FOR GENERATING A CONTRAST ENHANCEMENT MAP

TECHNICAL FIELD

The present document relates to a method and a system for generating a contrast enhancement map. In particular, it relates to a method and a system for generating a contrast enhancement map of a portion of a patient.

BACKGROUND

Medical Magnetic Resonance Imaging (MRI) is generally based on relaxation properties of excited hydrogen nuclei (protons) in water and fat of an object under test. When the object to be imaged is placed in a powerful, uniform magnetic field of an MRI scanner, the spins of the atomic nuclei of water in the object with non-integer spin numbers within the object all align either parallel to the magnetic field or anti-parallel. From an MR acquisition, several physical properties of the object under test can be determined with an absolute scale.

In order to understand MRI, it is important to know different time constants involved in the relaxation processes which establish equilibrium following RF excitation. As the excited protons relax and realign, they emit energy at rates which are recorded to provide information about their environment. The realignment of proton spins with the magnetic field is termed longitudinal relaxation and the rate ($s^{-1}$) required for a certain percentage of the object nuclei to realign is termed "longitudinal R1 relaxation rate" or R1. T2 weighted (T2W) imaging relies upon local dephasing of spins following the application of the transverse energy pulse; the transverse relaxation rate (typically >10 $s^{-1}$ for object) is termed "R2 relaxation rate" or R2. These relaxation rates are also expressed as relaxation times T1 (=1/R1) and T2 (=1/R2). The total signal depends on the number of protons, or proton density PD.

MRI contrast agents, such as gadolinium (GD) based contrast agent, are widely used as biomarkers to improve visibility of internal tissues of the object in MRI. For example, GD-based contrast agents are commonly used for brain tumour contrast enhancement associated with degradation or damage of the blood-brain-barrier, wherein the contrast of the lesions and tumours where the GD-based contrast agent is infiltrated through the damaged blood-brain-barrier, is enhanced.

Typically, a native T1 weighted (T1W) image of an objected before any contrast agent administration is acquired as a reference or a baseline. After a waiting time, typically 5 to 20 minutes following the contrast agent administration, a second T1W image of the same object is acquired to show potential infiltration of the contrast agent in the object as enhancement comparing with the native T1W image.

The doubled acquisitions are not only time-consuming, but also physically demanding for a patient. The patient has to stay motionless for a considerable time in the MR scanner from the first T1W image acquisition, during the contrast agent administration, until the second T1W image acquisition, to reduce the potential problems occurs during image co-registration caused by any displacement of the patient. Besides lying relatively still for 15 to 40 minutes, the patient has to endure all the noises created by the scanner itself during, e.g., altering magnetic fields, which obviously increases the discomfort for the patient.

Though skipping the native T1W image acquisition can alleviate the difficulties of the process, it inevitably decreases the analysis confidence, especially for anatomically complex portions of the patient, such as the brain.

Moreover, when using such T1W images, the signal intensity has an arbitrary scale, affected by the MR scanner's settings and imperfections, such as B1 inhomogeneity and coil sensitivity. Thus, when analysing the patient, the arbitrary scale, e.g., a signal intensity, not only leads to subjective reading of images, inherent inaccuracy and user dependence, but also being useless for quantitative analysis, such as an actual contrast agent concentration in the brain.

Though MRI brings many advantages in imaging technique, the time-consuming and uncomfortable process remains a problem. Therefore, there is a need for improvement.

SUMMARY

It is an object of the present disclosure, to provide an improved method and system for generating a contrast enhancement map of a portion of a patient, which eliminates or alleviates at least some of the disadvantages of the prior art.

According to a first aspect, there is provided a method for generating a contrast enhancement map of a portion of a patient, comprising acquiring a magnetic resonance, MR, quantification sequence of the portion, wherein the MR quantification sequence comprises quantification information of a longitudinal R1 relaxation rate, R1, and proton density, PD, of the portion, generating an R1 map of the portion based on the MR quantification sequence, wherein a value of R1 for each voxel of the R1 map is determined, generating a PD map of the portion based on the MR quantification sequence, wherein a value of PD for each voxel of the PD map is determined, estimating a R1' map of the portion, based on the PD map and a predetermined relationship of R1 and PD of the portion, wherein an estimated value of R1' for each voxel of the R1' map is calculated, generating a delta R1 map based on the R1 map and the R1' map, wherein the voxels of the R1 map, of the PD map, of the R1' map, and of the delta R1 map, have a one to one correspondence, wherein a value of each voxel of the delta R1 map represents a difference of R1 values of the corresponding voxel of the R1 map and of the corresponding voxel of the R1' map.

Hence, the present invention provides an improved method which shortens the time-consuming process of generating a contrast enhancement map by reducing the number of MR acquisitions. The accuracy of the contrast enhancement map is not comprised by using the estimated R1' map to represent a native or pre-contrast status of the portion, to compare with the post-contrast status of the portion representing changes of the portion, such as a contrast agent administration or a brain damage, such as a cerebral haemorrhage. Moreover, it is able to reduce the uncomfortableness for the patient by shortening the time of staying motionless inside of the MR scanner. Last but not least, it is able to provide a quantitative measure of the changes in the portion, such as a contrast agent concentration in the brain, which is valuable for analysing the portion of the patient.

An MR quantification sequence is an MR sequence comprising quantification information of physical properties of a portion of a patient, such as a slice of a brain. The physical properties may be longitudinal R1 relaxation rate (R1), transverse R2 relaxation rate (R2), proton density (PD), longitudinal T1 relaxation time (T1), and transverse T2 relaxation time (T2).

Based on the MR quantification sequence, maps of different physical properties can be generated, such as a R1 map or a PD map. Such a map comprises a plurality of voxels (in a 3D map) or pixels (in a 2D map). Each voxel of the map comprises at least a value with an absolute scale representing the physical property of a tiny portion of the patient corresponding to the voxel of the map.

With the maps of different physical properties, conventional MR images, such as a T1 weighted (T1W) image can be synthesized instead of acquiring by a MR scanner. Hereinafter, a synthesized image refers to images simulated based on the maps of physical properties of the portion of the patient, to distinguish from the conventional MR images acquired directly by the MR scanner.

The method may further comprise displaying the delta R1 map on a user interface.

Generating the delta R1 map comprises: for each voxel of the delta R1 map, calculating a value by subtracting a value of R1 of the corresponding voxel of the R1' map, from a value of R1 of the corresponding voxel of the R1 map.

The predetermined relationship of R1 and PD of the portion may be as the following formula R1=a+b*PD, wherein R1 is a value of R1, PD is a value of PD, and a and b are predetermined constants.

Estimating the R1' map may further comprise: for each voxel of the R1' map, calculating a value of R1 as the following formula Rt=a+b*PD, wherein R1' is a value of R1 of the voxel of the R1' map, PD is a value of PD of the corresponding voxel of the PD map, and a and b are the predetermined constants.

Generating the delta R1 map may further comprise: for each voxel of the delta R1 map, comparing a value of the voxel of the delta R1 map with a predetermined threshold, if the value of the voxel of the delta R1 map is less than the predetermined threshold, setting the value of the voxel of the delta R1 map to a predetermined value.

The predetermined value may be 0. The predetermined threshold may be 0.2 $S^{-1}$.

The method may further comprise: generating a synthetic MR image based on the R1 map and the PD map, and displaying the synthetic MR image in the user interface.

The method may further comprise: displaying the delta R1 map as an overlay over the synthetic MR image in the user interface.

Generating a synthetic MR image may further comprise: generating a synthetic T1 weighted, T1W, image of the portion, based on the R1 map and the PD map, comprising: for each voxel of the synthetic T1W image, estimating a signal strength S with the following formula S=PD·(1−exp(−R1·TR)), wherein S is a value of signal strength S of the voxel of the synthetic T1W image, PD is a value of PD of the corresponding voxel of the PD map, R1 is a value of R1 of the corresponding voxel of the R1' map, and TR is a repetition time.

The method may further comprise: estimating a synthetic T1W' image, based on the synthetic T1W image and the delta R1 map.

Estimating a synthetic T1W' image may further comprise: for each voxel of the synthetic T1W' image, calculating a value of signal strength S by subtracting a value of the corresponding voxel of the delta R1 map, from a value of signal strength S of the corresponding voxel of the synthetic T1W image.

The method may further comprise: generating a reference based on the portion to visualise a position of the delta R1 map relative to the reference, and displaying the reference in the user interface.

The reference may be an outline of a cross section of the portion, such as an outline of an intracranial volume of a brain.

The portion of the patient may be a head, extremity, torso, abdomen, pelvis or a specific organ.

The method may further comprise: administering a contrast agent into the patient, before acquiring the MR quantification sequence.

The contrast agent may comprise gadolinium-based contrast agent.

The method may further comprise: generating a contrast agent concentration image based on the delta R1 map.

According to a second aspect, there is provided a system for generating a contrast enhancement map of a portion of a patient, comprising: an MR scanning device configured to: acquire a magnetic resonance, MR, quantification sequence of the portion, wherein the MR quantification sequence comprises quantification information of a longitudinal R1 relaxation rate, R1, and proton density, PD, of the portion, a processing circuit configured to: generate an R1 map of the portion based on the MR quantification sequence, wherein a value of R1 for each voxel of the R1 map is determined, generate a PD map of the portion based on the MR quantification sequence, wherein a value of PD for each voxel of the PD map is determined, estimate a R1' map of the portion, based on the PD map and a predetermined relationship of R1 and PD of the portion, wherein an estimated value of R1' for each voxel of the R1' map is calculated, generate a delta R1 map based on the R1 map and the R1' map, wherein the voxels of the R1 map, of the PD map, of the R1' map, and of the delta R1 map, have a one to one correspondence, wherein a value of each voxel of the delta R1 map represents a difference of R1 values of the corresponding voxel of the R1 map and of the corresponding voxel of the R1' map.

The processing circuit may perform the processes described herein.

The processing circuit may comprise one or many processors. The processor(s) may be implemented by a single dedicated processor, by a single shared processor, or by a plurality of individual processors, some of which may be shared or distributed.

The processing circuit may comprise a microcontroller, a digital signal processor (DSP), a general purpose processor, CPU, ASIC, read only memory (ROM), random access memory (RAM), and/or other storage media.

The system may further comprise: a user interface configured to display the delta R1 map.

The processing circuit may be further configured to: for each voxel of the delta R1 map, calculate a value by subtracting a value of R1 of the corresponding voxel of the R1' map, from a value of R1 of the corresponding voxel of the R1 map.

The predetermined relationship of R1 and PD of the portion is as the following formula R1=a+b*PD, wherein R1 is a value of R1, PD is a value of PD, and a and b are predetermined constants.

The processing circuit may be further configured to: for each voxel of the R1' map, calculate a value of R1 as the following formula R1'=a+b*PD, wherein R1' is a value of R1 of the voxel of the R1' map, PD is a value of PD of the corresponding voxel of the PD map, and a and b are the predetermined constants.

The processing circuit may be further configured to: for each voxel of the delta R1 map, compare a value of the voxel of the delta R1 map with a predetermined threshold, if the value of the voxel of the delta R1 map is less than the predetermined threshold, setting the value of the voxel of the delta R1 map to a predetermined value.

The predetermined value may be 0. The predetermined threshold may be 0.2 S$^{-1}$.

The processing circuit may be further configured to: generate a synthetic MR image based on the R1 map and the PD map, and the user interface is further configured to display the synthetic MR image.

The user interface may be further configured to display the delta R1 map as an overlay over the synthetic MR image in the user interface.

The processing circuit may be further configured to: generate a synthetic T1 weighted, T1W, image of the portion, based on the R1 map and the PD map, comprising: for each voxel of the synthetic T1W image, estimate a signal strength S with the following formula S=PD·(1−exp(−R1·TR)), wherein S is a value of signal strength S of the voxel of the synthetic T1W image, PD is a value of PD of the corresponding voxel of the PD map, R1 is a value of R1 of the corresponding voxel of the R1' map, and TR is a repetition time.

The processing circuit may be further configured to: estimate a synthetic T1W' image, based on the synthetic T1W image and the delta R1 map.

The processing circuit may be further configured to: for each voxel of the synthetic T1W' image, calculate a value of signal strength S by subtracting a value of the corresponding voxel of the delta R1 map, from a value of signal strength S of the corresponding voxel of the synthetic T1W image.

The processing circuit may be further configured to: generate a reference based on the portion to visualise a position of the delta R1 map relative to the reference, and the user interface is further configured to display the reference.

The reference may be an outline of a cross section of the portion, such as an outline of an intracranial volume of a brain.

The portion of the patient may be a head, extremity, torso, abdomen, pelvis or a specific organ.

According to a third aspect, there is provided a method of identifying a pathological condition in a patient, comprising: identifying the pathological condition based on the delta R1 map generated by the method of the first aspect.

The method may further comprise: identifying a pathological region of the patient based on the delta R1 map generated by the method of the first aspect. The pathological region may be identified by a difference in values for adjacent voxels.

The method may further comprise administering a contrast agent into the patient, before acquiring the MR quantification sequence, wherein the pathological region is infiltrated by a greater amount of the contrast agent than adjacent, non-pathological regions.

According to a fourth aspect, there is provided a system for identifying a pathological condition in a patient, comprising: a processing circuit configured to: identify the pathological condition based on the delta R1 map generated by the system of the second aspect.

The processing circuit may be further configured to: identifying a pathological region of the patient based on the delta R1 map generated by the system of the second aspect. The pathological region may be identified by a difference in values for adjacent voxels.

BRIEF DESCRIPTION OF THE DRAWINGS

FIG. 2b is a synthetic T1W image generated based on an MR quantification sequence acquired after the GD-based contrast agent administration of the same slice in FIG. 2a.

FIG. 2c is a R1 map generated based on the MR quantification sequence acquired before the GD-based contrast agent administration of the same slice in FIG. 2a.

FIG. 2d is a R1 map generated based on the MR quantification sequence acquired after the GD-based contrast agent administration of the same slice in FIG. 2a.

FIG. 2f is a delta R1 map generated based on the MR sequence acquired after the GD-based contrast agent administration of the same slice in FIG. 2a.

FIG. 3a is a zoomed part around the malignant glioma in the synthetic T1W image of FIG. 2a.

FIG. 4b is a synthetic T1W image generated based on an MR quantification sequence acquired after the GD-based contrast agent administration, of the same slice in FIG. 4a.

FIG. 4d is a delta R1 map generated based on the MR quantification sequence acquired after the GD-based contrast agent administration of the same slice in FIG. 4a.

DESCRIPTION OF EMBODIMENTS

Figure 5:
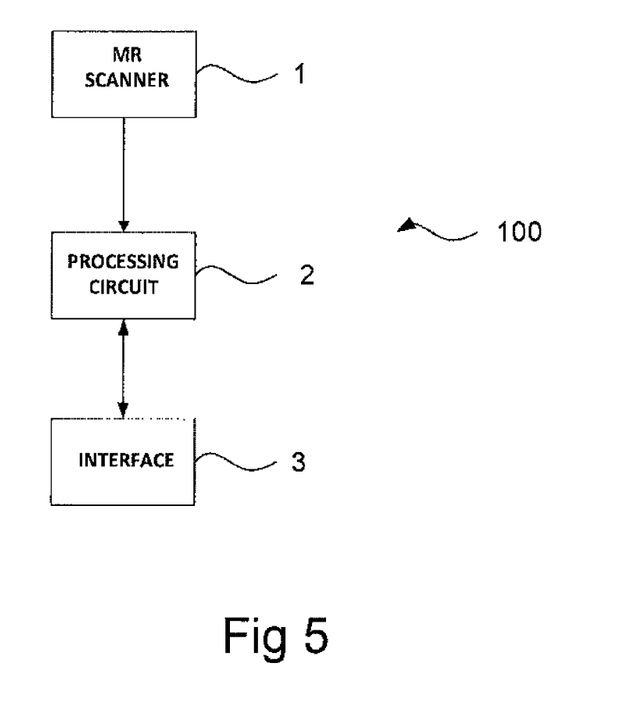
FIG. 5 is a schematic outline of a system for generating a contrast enhancement map of a portion of a patient.

In FIG. 5, a general view of a system 100 for generating a contrast enhancement map of a portion of a patient is depicted. The system 100 may comprise an MR scanning device 1 and a processing circuit 2.

The MR scanning device 1 may be configured to acquire MR information by scanning an object under test, such as a portion of a patient. The MR scanning device 1 may acquire an MR quantification sequence of the portion. The acquired MR quantification sequence may comprise quantification information of the portion, such as R1 and PD of the portion.

The MR scanning device 1 may be connected to the processing circuit 2 for processing the MR quantification sequence acquired by the MR scanning device 1. In particular, the processing circuit 2 may perform the processes as described herein.

The processing circuit 2 may be connected to a user interface 3. The user interface 3 may receive and/or output data and information. The user interface 3 may receive input, such as a command, information or data, from one or several input devices. The input device may be a computer mouse, a keyboard, a track ball, a touch screen, or any other input device. The user interface 3 may send the received input to the processing circuit 2 for further processing. The user interface 3 may output and/or display an image, map, data, or information.

A physical property map of a portion of a patient can be generated based on an MR quantification sequence, e.g., acquired by the MR scanning device 1. The processing circuit 2 may generate different maps based on the acquired MR quantification sequence. Through different maps, quantitative physical properties, such as R1, R2, PD, T1, T2, of the portion, may be individually shown. Each voxel of one map comprises a value with an absolute scale representing a physical property of a tiny portion of the patient corresponding to the voxel. Thus, a R1 map of the portion comprises a plurality of voxels each comprising a R1 value, and a PD map of the same portion comprises a plurality of voxels each comprising a PD value.

Since both the R1 map and PD map are generated based on the same MR quantification sequence, the voxels of the R1 map and of the PD map have a one to one correspondence. The one to one correspondence of the voxels between different maps is advantageous such that a co-registration between different maps and/or synthetic images is no longer necessary when co-relating the maps and/or synthetic images.

For each voxel in the R1 map, its R1 value is known. For its corresponding voxel in the PD map, the PD value is known. Thus, each voxel in the R1 map can be associated to the known PD value of its corresponding voxel in the PD map. That is, each voxel of the R1 map or of the PD map corresponds to two known values, i.e. the R1 value and the PD value.

Figure 1A:
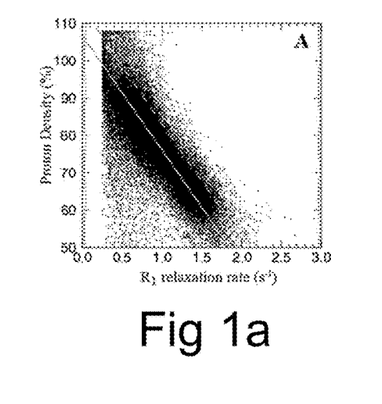
FIG. 1a shows PD values as a function of R1 values of a slice of a brain diagnosed with malignant glioma, at 3 Tesla, before a GD-based contrast agent administration.

Thus, it provides a possibility to correlate the PD values and R1 values of the respective PD map and R1 map by plotting the PD value as a function of R1 value for each voxel of the R1 map or of the PD map, as FIG. 1a.

In FIG. 1a, the x-axis is R1 ($s^{-1}$) and the y-axis is PD (%), wherein the PD values generated based on the MR quantification sequence acquired before the GD-based contrast agent administration are plotted, e.g., by the processing circuit 2, as a function of the corresponding R1 values, of the slice of the brain at 3 Tesla. Each point in FIG. 1a represents one voxel in the R1 map, and one voxel in the PD map, wherein the projected value of the point on the x-axis is the R1 value of the voxel and the projected value of the point on the y-axis is the PD value of the voxel. It is also possible to use e.g., 1.5 Tesla and 2 Tesla.

By integrating the R1 and PD quantification information of the slice of the brain into one figure, the R1 and PD quantification information of all the matters of the slice of the brain, including the white matter, the grey matter, the water, etc., may be represented in FIG. 1a.

A R1-PD relationship may be derived, e.g., by the processing circuit 2, based on FIG. 1a. The R1-PD relationship may be an average of all the matters of the slice of the brains, i.e. an average of all the points in FIG. 1a. The R1-PD relationship may be a R1-PD relationship of only the grey and white matter in the slice. The R1-PD relationship may be a substantial linear relationship.

In FIG. 1a, the solid line represents an average R1-PD relationship of the grey and white matter in the slice of the brain. The R1-PD relationship may be as the following formula (1)

$$R1 = a + b*PD \qquad \text{formula (1)}$$

R1, PD, a and b in formula (1) respectively represent a value of R1, a value of PD, and predetermined constants.

The constants a and b may be determined based on many factors, such as, which portion of the patient it is and different instrument parameters. Different constants a and b may be chosen to reflect a different R1-PD relationship for the exact portion of the patient under test.

Taking a slice of brain as an example, before any contrast agent administration, at 3 Tesla, a cortical grey matter can be positioned at R1=0.77 $s^{-1}$ and PD at 86.88% and a white matter can be positioned at R1=1.38 $s^{-1}$ and PD at 65.60%. Mathematically, every 1% change of the PD value is associated with a 0.029 $s^{-1}$ change of R1 value. Thus, an intercept of the x-axis (R1) is 3.29. Accordingly, the constants a and b are 3.29 and −0.029, respectively. A R1 value according to the predetermined R1-PD relationship of the slice of brain, e.g., the solid line in FIG. 1a, can be estimated by the following formula (2), e.g., by the processing circuit 2.

$$R1 = 3.29 - 0.029*PD \qquad \text{formula (2)}$$

The administration of a contrast agent into the patient, such as the GD-based contrast agent, may result in that the lesions exhibit a strong decrease of the longitudinal T1 relaxation time or, equivalently, increase of the longitudinal R1 relaxation rate (R1=1/T1). Hence, after the GD-based contrast agent administration, the observed R1 in the lesions will be increased.

Figure 1B:
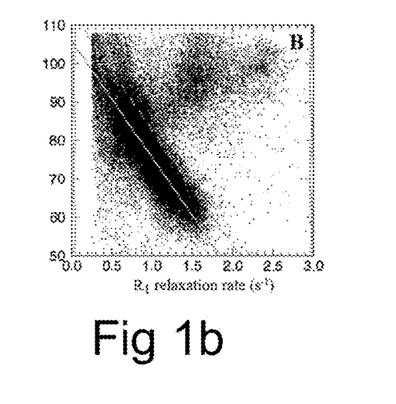
FIG. 1b shows PD values as a function of R1 values of the same slice of the brain at, 3 Tesla, after the GD-based contrast agent administration.

FIG. 1b shows the PD values generated based on the MR quantification sequence acquired after the GD-based contrast agent administration as a function of R1 values of the same portion as in FIG. 1a. In FIG. 1b, some R1 values, which belong to the voxels corresponding to the malignant glioma, are substantially increased due to the administered GD-based contrast agent. The rest part of the slice of the brain is relatively unchanged because only the lesion part, i.e. the malignant glioma, will result in a higher R1 value after the GD-based contrast agent administration. Comparing FIGS. 1a and 1b, besides those voxels having increased R1 values, most voxels having unchanged R1 values before and after the GD-based contrast agent administration. That is, the R1-PD relationships of FIGS. 1a and 1b may be the same. Thus, in FIG. 1b, the solid line represents the same R1-PD relationship of the slice of the brain as the one in FIG. 1a.

Thus, it provides a possibility to estimate a R1' map of the slice of the brain representing a pre-contrast status of the portion before the GD-based contrast agent administration, based only on the known R1-PD relationship and the PD map generated based on the MR quantification sequence acquired after the GD-based contrast agent administration.

This is beneficial since it is not necessary to acquire any MR quantification sequence, e.g., by the MR scanning device 1, before the GD-based contrast agent administration, to generate a R1' map, e.g., by the processing circuit 2, as a reference or baseline, to compare, e.g., by the processing circuit 2, with the changed R1 map as a result of the GD-based contrast agent administration.

For each voxel of the R1' map, a R1 value may be calculated, e.g., by the processing circuit 2, based on the known R1-PD relationship and the PD value of the corresponding voxel in the PD map generated based on the acquired MR quantification sequence after the GD-based contrast agent administration. The R1 value of a voxel of the R1' map maybe calculated as the following formula (3), e.g., by the processing circuit 2.

$$R1' = a + b*PD \qquad \text{formula (3)}$$

R1', PD, a and b in formula (3) are respectively a value of R1 of the voxel of the R1' map, a value of PD of the corresponding voxel of the PD map, a and b are the predetermined constants.

After estimated the R1' map of the portion, a delta R1 map of the portion can be generated, e.g., by the processing circuit 2, based on the estimated R1' map and the R1 map generated based on the MR quantification sequence acquired after the GD-based contrast agent administration. Since the voxels of these two R1 maps have a one to one correspondence, the delta R1 map can be generated by "subtracting" the estimated R1' map from the R1 map, e.g., by the processing circuit 2, to reflect a difference of R1 values as a result of the GD-based contrast agent administration. That is, each voxel of the delta R1 map represents a difference of R1 values of the tiny portion of the brain corresponding to the voxel before and after the GD-based contrast agent administration.

For each voxel of the delta R1 map, a value can be calculated as the following formula (4), e.g., by the processing circuit 2.

$$\text{Delta } R1 = R1 - (a + b*PD) \qquad \text{formula (4)}$$

Delta R1, R1, PD, a and b in formula (4) are respectively a value of R1 of the voxel of the delta R1 map, a value of R1 of the corresponding voxel of the R1 map, a value of PD of the corresponding voxel of the PD map, a and b are the predetermined constants.

With the differences of the R1 values, the delta R1 map may be used as a contrast enhancement map of the portion of the patient to visualise any change caused by the contrast agent administration. Although the examples so far discuss only the R1 differences as a result of the GD-based contrast agent administration, it is not necessary to have any contrast agent administered into the patient. It may be used to visualise contrast enhancement as a result of other types of changes in the portion of the patient, e.g., a brain damage, a bleeding in the brain such as cerebral haemorrhage. Thus, the contrast enhancement as a result of different types of changes in the portion of the patient can be visualised with the method and/or the system of the present application.

A predetermined threshold may be applied, e.g., by the processing circuit 2, when generating the delta R1 map. The predetermined threshold may be used to suppress the noise in the delta R1 map, such as a system noise, an environmental noise, or a bad measuring, and to increase the accuracy of the delta R1 map.

For each voxel of the delta R1 map, the value of the voxel, i.e. the differences of R1 values of the corresponding voxels in the R1 map and the R1' map, may be compared, e.g., by the processing circuit 2, with the predetermined threshold. If the value of the voxel of the delta R1 map is less than the predetermined threshold, the value of the voxel of the delta R1 map may be set to a predetermined value, e.g., by the processing circuit 2. The predetermined value may be 0. The predetermined threshold may be 0.2 s$^{-1}$, as the dashed line in FIGS. 1a and 1b.

Accordingly, the voxels of the delta R1 map having a value of R1 differences being less than the predetermined threshold, e.g., 0.2 s$^{-1}$, may be considered as "noise" and to be removed by setting to a predetermined value, such as 0.

The predetermined value could be e.g., 0.1, 0.05, 0.01, 0.001, etc. By setting a value of a voxel to a reduced value, the noise caused by this voxel can be suppressed and the accuracy of the delta R1 map can be increased.

Thus, the system noise, the environmental noise, and even a bad measurement can be removed to create a more accurate delta R1 map.

The portion of the patient may be a head, extremity, torso, abdomen, pelvis or a specific organ. The portion may be a pathological body portion.

The GD-based contrast agent concentration can also be derived from the delta R1 map, e.g., by the processing circuit 2. For example, the GD-based contrast agent concentration can be derived from the delta R1 map by using a predetermined calibration constant, e.g., by the processing circuit 2.

Based on the R1 map and PD map of the portion, conventional MR images, such as a T1W image, can be simulated, e.g., by the processing circuit 2, instead of acquiring by the MR scanning device 1. Thus, a synthesized T1W image may be simulated, e.g., by the processing circuit 2, based on the R1 map and PD map of the portion generated based on the acquired MR quantification sequence. On the contrary, the conventional T1W images have to be acquired by scanning the portion of the patient with the MR scanning device 1.

Figure 2A:
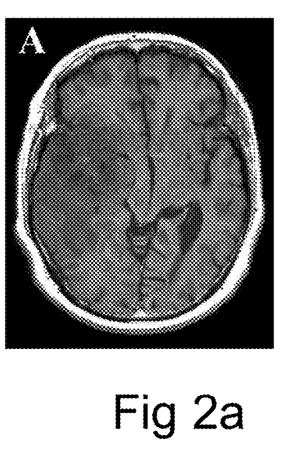
FIG. 2a is a synthetic T1W image generated based on an MR quantification sequence acquired before a GD-based contrast agent administration, of an axial slice of a patient's brain diagnosed with malignant glioma.
Figure 2B:
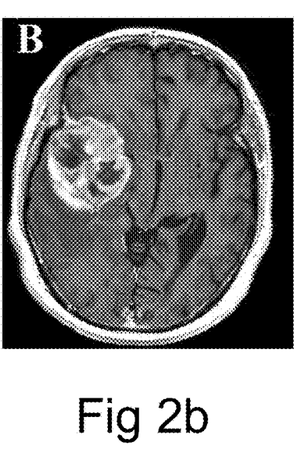
Figure 2C:
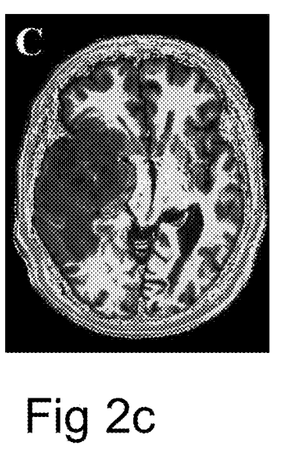

FIGS. 2a and 2c are respectively a synthetic T1W image and a R1 map, generated, e.g., by the processing circuit 2, based on an MR quantification sequence acquired, e.g., by the MR scanning device 1, before a GD-based contrast agent administration, of an axial slice of a patient's brain diagnosed with malignant glioma. Thus, FIGS. 2a and 2c represent a native or pre-contrast status of the slice of the brain before the GD-based contrast agent administration.

The synthetic T1W image of the portion in FIG. 2a may be generated, e.g., by the processing circuit 2, based on the R1 map and the PD map, which are generated based on the MR quantification sequence acquired before the GD-based contrast agent administration. The voxels of the synthetic T1W image, of the R1 map, and of the PD map, have a one to one correspondence.

For each voxel of the synthetic T1W image, a signal strength S may be estimated with the following formula (5), e.g., by the processing circuit 2.

$$S = PD \cdot (1 - \exp(-R1 \cdot TR)) \qquad \text{formula (5)}$$

S, PD, R1 and TR of the formula (5) respectively represent a value of signal strength S of the voxel of the synthetic T1W image, a value of PD of the corresponding voxel of the PD map, a value of R1 of the corresponding voxel of the R1 map, and the repetition time.

Figure 2D:
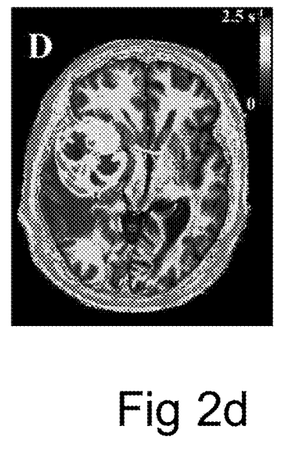

FIG. 2d is a R1 map generated e.g., by the processing circuit 2, based on an MR sequence acquired, e.g., by the MR scanning device 1, after the GD-based contrast agent administration of the same slice in FIG. 2a. Thus, FIG. 2d represents a post-contrast status of the slice of the brain after the GD-based contrast agent administration.

FIG. 2b is a synthetic T1W image generated e.g., by the processing circuit 2, based on the MR quantification sequence acquired after the GD-based contrast agent administration of the same slice in FIG. 2a. Thus, FIG. 2b represents a post-contrast status of the same slice of the brain after the GD-based contrast agent administration.

By co-registration R1 maps in FIGS. 2c and 2d, e.g., by the processing circuit 2, a map of R1 differences of the slice of the brain as a result of the GD-based contrast agent administration is achieved, based on the MR quantification sequences acquired before and after the GD-based contrast agent. The highlighted part in FIG. 2e comprises the voxels having increased R1 values as a result of the GD-based contrast agent administration. That is, the highlighted part in FIG. 2e may correspond to the malignant glioma in the slice of the brain. However, at least two MR quantification sequences are needed to generate FIG. 2e, i.e. one MR quantification sequence acquired before and one acquired after the GD-based contrast agent administration.

Figure 2E:
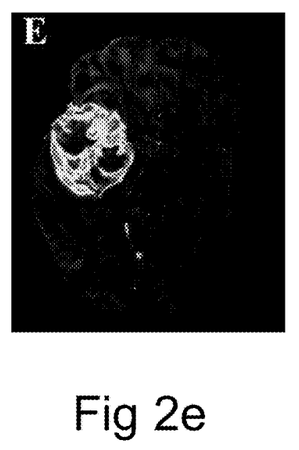
FIG. 2e is a map of R1 differences of the co-registered R1 maps in FIGS. 2c and 2d.
Figure 2F:
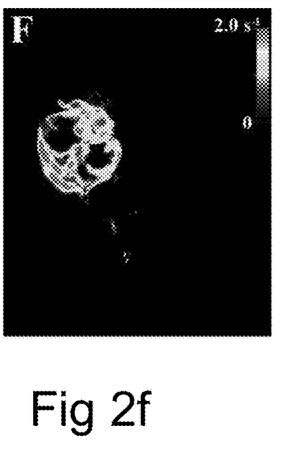

FIG. 2f is a delta R1 map generated, e.g., by the processing circuit 2, based only on the MR quantification sequence acquired, e.g., by the MR scanning device 1, after the GD-based contrast agent administration of the same slice in FIG. 2a. First, the R1' map (not shown) of the portion representing the pre-contrast status of the slice of the brain before the GD-based contrast agent administration can be generated, based only on the MR quantification sequence acquired after the GD-based contrast agent administration. Then, FIG. 2f can be generated by "subtracting" the R1' map (not shown) from the R1 map of FIG. 2d, as described above, e.g., by the processing circuit 2.

The delta R1 map generated, e.g., by the processing circuit 2, based only on the MR quantification sequence acquired after the GD-based contrast agent administration in FIG. 2f shows not only a high fidelity comparing to FIG. 2e which is generated based on doubled MR quantification acquisitions, but also a higher contrast between the abnormal portion, i.e. the malignant glioma, and the normal portion of the slice of the brain.

Figure 3A:
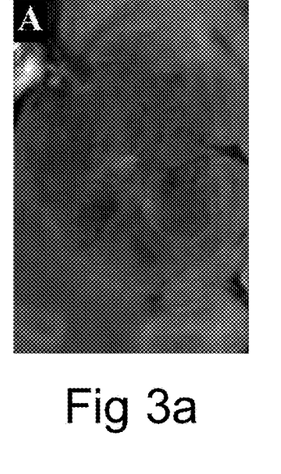

FIG. 3a is a zoomed part around the malignant glioma in the synthetic T1W image of FIG. 2a, which represents a pre-contrast status of the malignant glioma before the GD-based contrast agent administration.

Figure 3B:
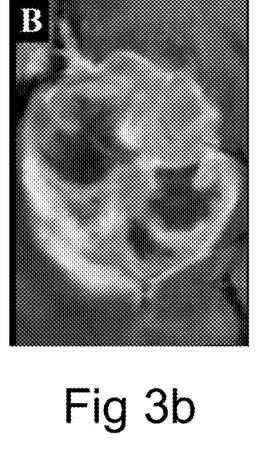
FIG. 3b is a zoomed part around the malignant glioma in the synthetic T1W image of FIG. 2b.

FIG. 3b is a zoomed part around the malignant glioma in the synthetic T1W image of FIG. 2b, which represents a post-contrast status of the malignant glioma after the GD-based contrast agent administration. Comparing with FIG. 3a, it is clear that the malignant glioma in FIG. 3b is enhanced as a result of the GD-based contrast agent administration.

Figure 3C:
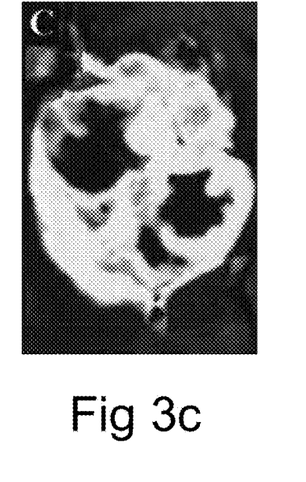
FIG. 3c is FIG. 3b with a zoomed part around the malignant glioma of the delta R1 map of FIG. 2f as an overlay.

FIG. 3c is FIG. 3b with a zoomed part around the malignant glioma of the delta R1 map of FIG. 2f as an overlay. The overlay can have a color different from that of the FIG. 3b to improve visibility of the interested part of the portion, e.g. the malignant glioma. For example, in FIG. 3c, the overlay is in a green colour.

FIG. 3c also comprises a reference, i.e. a red line, indicating an edge of an intracranial volume of the slice of the brain. The reference may visualise a relative position of the malignant glioma in the brain. The reference may also be an outline of a cross section of the portion of the patient, such as an outline of an intracranial volume of a brain.

The reference may be generated, e.g., by the processing circuit 2, by known techniques, such as tissue recognition, MR image processing, etc.

Figure 4A:
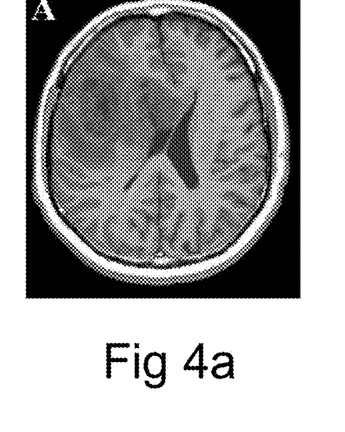
FIG. 4a is a synthetic T1W image generated based on an MR quantification sequence acquired before a GD-based contrast agent administration of a slice of a patient's brain.

FIG. 4a is a synthetic T1W image generated, e.g., by the processing circuit 2, based on an MR quantification sequence acquired, e.g., by the MR scanning device 1, before a GD-based contrast agent administration of a slice of a patient's brain. FIG. 4a represents a pre-contrast status of the slice of the brain.

Figure 4B:
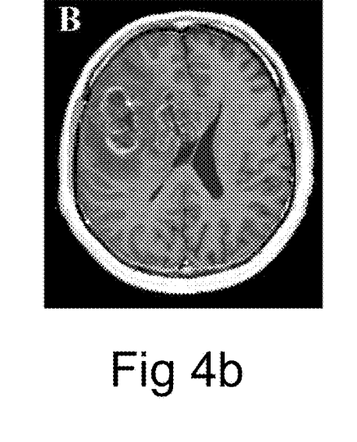

FIG. 4b is a synthetic T1W image generated e.g., by the processing circuit 2, based on an MR quantification sequence acquired, e.g., by the MR scanning device 1, after the GD-based contrast agent administration, of the same slice in FIG. 4a. FIG. 4b represents a post-contrast status of the slice of the brain, wherein R1 values of the voxels corresponding to a pathological part of the brain are enhanced as a result of the GD-based contrast agent administration.

Figure 4C:
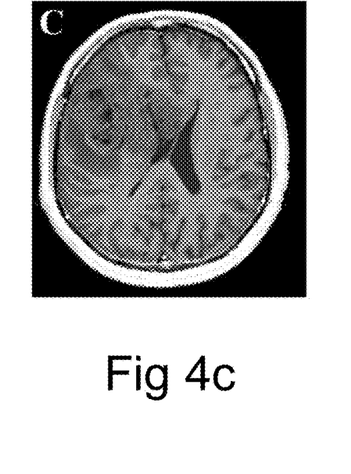
FIG. 4c is a synthetic T1W' image representing the same slice in FIG. 4a of the patient before the GD-based contrast agent administration, generated based on the MR quantification sequence acquired after the GD-based contrast agent administration.
Figure 4D:
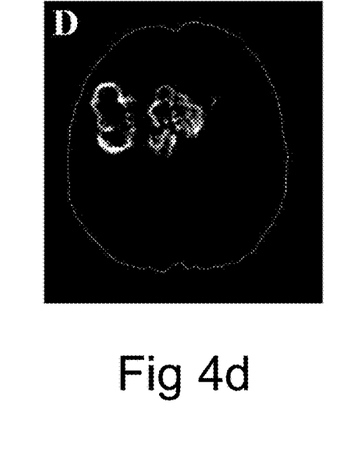

FIG. 4d is a delta R1 map generated, e.g., by the processing circuit 2, based on the MR quantification sequence acquired after the GD-based contrast agent administration of the same slice in FIG. 4a. The highlighted part of the brain in FIG. 4d visualise the pathological part of the brain.

In FIG. 4d, a reference is generated, e.g., by the processing circuit 2, based on the slice of the brain to visualize a relative position of the highlighted pathological part in the brain. The reference may be used as a visual aid. The reference may be an outline of an intracranial volume of the slice of the brain, as in FIG. 4d. The reference may also be an outline of a cross section of the portion of the patient.

The reference may be generated by known techniques, such as tissue recognition, MR image processing, etc.

FIG. 4c is a synthetic T1W' image representing the portion of the patient before the GD-based contrast agent administration, generated, e.g., by the processing circuit 2, based on the MR quantification sequence acquired after the GD-based contrast agent administration.

For example, the synthetic T1W' image can be generated, e.g., by the processing circuit 2, by a "subtraction" of the delta R1 map in FIG. 4d from the synthetic T1W image in FIG. 4b.

The synthetic T1W' image generated, e.g., by the processing circuit 2, based only on the MR quantification sequence acquired after the contrast agent administration in FIG. 4c shows a high fidelity comparing to FIG. 4a which is generated based on the MR quantification sequence acquired before the contrast agent administration. Thus, it provides a possibility to synthesize a T1W' image representing the pre-contrast status based only the MR quantification sequence acquired after the contrast agent administration.

The "subtraction" can be implemented, e.g., by the processing circuit 2, in a voxel level. For each voxel of the synthetic T1W' image, a value of signal strength S of the voxel of the synthetic T1W' image is calculated by subtracting a value of R1 differences of the corresponding voxel of the delta R1 map, from a value of signal strength S of the corresponding voxel of the synthetic T1W image.

The invention claimed is:
1. A method for generating a contrast enhancement map of a portion of a patient, comprising:
   acquiring, by an MR scanner, a magnetic resonance (MR) quantification sequence of the portion, wherein the MR quantification sequence comprises quantification information of a longitudinal relaxation rate R1 and proton density (PD) of the portion,
   generating, by a processing circuit, an R1 map of the portion based on the MR quantification sequence, wherein a value of R1 for each voxel of the R1 map is determined,
   generating, by the processing circuit, a PD map of the portion based on the same MR quantification sequence used to generate the R1 map, wherein a value of PD for each voxel of the PD map is determined,
   estimating, by the processing circuit, a R1' map of the portion, based on the PD map and a predetermined relationship of R1 and PD of the portion, wherein an estimated value of R1' for each voxel of the R1' map is calculated,
   generating, by the processing circuit, a delta R1 map based on the R1 map and the R1' map,
   wherein the voxels of the R1 map, of the PD map, of the R1' map, and of the delta R1 map, have a one to one correspondence, wherein a value of each voxel of the delta R1 map represents a difference of R1 values of the corresponding voxel of the R1 map and of the corresponding voxel of the R1' map, and the method further comprises:

generating a synthetic MR image based on the R1 map and the PD map, displaying the synthetic MR image in the user interface, wherein generating a synthetic MR image further comprises:

generating a synthetic T1 weighted (T1W) image of the portion, based on the R1 map and the PD map, comprising:

for each voxel of the synthetic T1W image, estimating a signal strength S with the following formula $$S=PD \cdot (1-\exp(-R1 \cdot TR)),$$

wherein S is a value of signal strength S of the voxel of the synthetic T1W image, PD is a value of PD of the corresponding voxel of the PD map, R1 is a value of R1 of the corresponding voxel of the R1' map, and TR is a repetition time.

2. The method as claimed in claim 1, further comprising: displaying the delta R1 map on a user interface.

3. The method as claimed in claim 1, wherein generating the delta R1 map comprises:

for each voxel of the delta R1 map, calculating a value by subtracting a value of R1 of the corresponding voxel of the R1' map, from a value of R1 of the corresponding voxel of the R1 map.

4. The method as claimed in claim 1, wherein the predetermined relationship of R1 and PD of the portion is as the following formula R1=a+b*PD, wherein R1 is a value of R1, PD is a value of PD, and a and b are predetermined constants.

5. The method as claimed in claim 4, wherein estimating the R1' map, further comprises:

for each voxel of the R1' map, calculating a value of R1 as the following formula $$R1'=a+b*PD,$$

wherein R1' is a value of R1' of the voxel of the R1' map,

PD is a value of PD of the corresponding voxel of the PD map, and a and b are the predetermined constants.

6. The method as claimed in claim 1, wherein generating the delta R1 map further comprises:

for each voxel of the delta R1 map, comparing a value of the voxel of the delta R1 map with a predetermined threshold, if the value of the voxel of the delta R1 map is less than the predetermined threshold, setting the value of the voxel of the delta R1 map to a predetermined value.

7. The method as claimed in claim 6, wherein the predetermined value is 0, and/or the predetermined threshold is 0.2 S−1.

8. The method as claimed in claim 1, further comprising:

displaying the delta R1 map as an overlay over the synthetic MR image in the user interface.

9. The method as claimed in claim 1, further comprising:

estimating a synthetic T1W' image, based on the synthetic T1W image and the delta R1 map.

10. The method as claimed in claim 9, wherein estimating a synthetic T1W' image further comprises:

for each voxel of the synthetic T1W' image, calculating a value of signal strength S by subtracting a value of the corresponding voxel of the delta R1 map, from a value of signal strength S of the corresponding voxel of the synthetic T1W image.

11. The method as claimed in claim 1, further comprising:

generating a reference based on the portion to visualise a position of the delta R1 map relative to the reference, and displaying the reference in the user interface.

12. The method as claimed in claim 11, wherein the reference is an outline of a cross section of the portion including an outline of an intracranial volume of a brain.

13. The method as claimed in claim 1, wherein the portion of the patient is a head, extremity, torso, abdomen, pelvis or a specific organ.

14. The method as claimed in claim 1, further comprising:

administering a contrast agent into the patient, before acquiring the MR quantification sequence.

15. The method as claimed in claim 14, wherein the contrast agent comprises gadolinium-based contrast agent.

16. The method as claimed in claim 14, further comprising:

generating a contrast agent concentration image based on the delta R1 map.

17. A system for generating a contrast enhancement map of a portion of a patient, comprising:

an MR scanner configured to:

acquire a magnetic resonance (MR) quantification sequence of the portion, wherein the MR quantification sequence comprises quantification information of a longitudinal relaxation rate R1 and proton density (PD) of the portion, a processing circuit configured to:

generate an R1 map of the portion based on the MR quantification sequence, wherein a value of R1 for each voxel of the R1 map is determined, generate a PD map of the portion based on the same MR quantification sequence used to generate the R1 map, wherein a value of PD for each voxel of the PD map is determined, estimate a R1' map of the portion, based on the PD map and a predetermined relationship of R1 and PD of the portion, wherein an estimated value of R1' for each voxel of the R1' map is calculated, generate a delta R1 map based on the R1 map and the R1' map, wherein the voxels of the R1 map, of the PD map, of the R1' map, and of the delta R1 map, have a one to one correspondence, wherein a value of each voxel of the delta R1 map represents a difference of R1 values of the corresponding voxel of the R1 map and of the corresponding voxel of the R1' map, wherein the processing circuit is further configured to:

generate a synthetic MR image based on the R1 map and the PD map, the user interface is further configured to display the synthetic MR image, generate a synthetic T1 weighted (T1W) image of the portion, based on the R1 map and the PD map, comprising:

for each voxel of the synthetic T1W image, estimate a signal strength S with the following formula $$S=PD \cdot (1-\exp(-R1 \cdot TR)),$$

wherein S is a value of signal strength S of the voxel of the synthetic T1W image, PD is a value of PD of the corresponding voxel of the PD map, R1 is a value of R1 of the corresponding voxel of the R1' map, and TR is a repetition time.

18. The system as claimed in claim 17, further comprising:

a user interface configured to display the delta R1 map.

19. The system as claimed in claim 17, wherein the processing circuit is further configured to:

for each voxel of the delta R1 map, calculate a value by subtracting a value of R1 of the corresponding voxel of the R1' map, from a value of R1 of the corresponding voxel of the R1 map.

20. The system as claimed in claim 17, wherein the predetermined relationship of R1 and PD of the portion is as the following formula R1=a+b*PD, wherein R1 is a value of R1, PD is a value of PD, and a and b are predetermined constants.

21. The system as claimed in claim 20, wherein the processing circuit is further configured to:

for each voxel of the R1' map, calculate a value of R1 as the following formula $$R1'=a+b*PD,$$

wherein R1' is a value of R1' of the voxel of the R1' map,

PD is a value of PD of the corresponding voxel of the PD map, and a and b are the predetermined constants.

22. The system as claimed in claim 17, wherein the processing circuit is further configured to:

for each voxel of the delta R1 map, compare a value of the voxel of the delta R1 map with a predetermined threshold, if the value of the voxel of the delta R1 map is less than the predetermined threshold, setting the value of the voxel of the delta R1 map to a predetermined value.

23. The system as claimed in claim 22, wherein the predetermined value is 0 and/or the predetermined threshold is 0.2 S−1.

24. The system as claimed in claim 17, wherein the user interface is further configured to display the delta R1 map as an overlay over the synthetic MR image in the user interface.

25. The system as claimed in claim 17, wherein the processing circuit is further configured to:

estimate a synthetic T1W' image, based on the synthetic T1W image and the delta R1 map.

26. The system as claimed in claim 25, wherein the processing circuit is further configured to:

for each voxel of the synthetic T1W' image, calculate a value of signal strength S by subtracting a value of the corresponding voxel of the delta R1 map, from a value of signal strength S of the corresponding voxel of the synthetic T1W image.

27. The system as claimed in claim 17, wherein the processing circuit is further configured to:

generate a reference based on the portion to visualise a position of the delta R1 map relative to the reference, and the user interface is further configured to display the reference.

28. The system as claimed in claim 27, wherein the reference is an outline of a cross section of the portion including an outline of an intracranial volume of a brain.

29. The system as claimed in claim 17, wherein the portion of the patient is a head, extremity, torso, abdomen, pelvis or a specific organ.

30. A method of identifying a pathological condition in a patient, comprising:

identifying the pathological condition based on the delta R1 map generated by the method of claim 1.

31. The method as claimed in claim 30, further comprising:

identifying a pathological region of the patient based on the delta R1 map, wherein the pathological region is identified by a difference in values for adjacent voxels.

32. The method as claimed in claim 31, further comprising administering a contrast agent into the patient, before acquiring the MR quantification sequence, wherein the pathological region is infiltrated by a greater amount of the contrast agent than adjacent, non-pathological regions.

33. A system for identifying a pathological condition in a patient, comprising:

a processing circuit configured to:

identify the pathological condition based on the delta R1 map generated by the system of claim 17.

34. A system for identifying a pathological condition in a patient, wherein the processing circuit is further configured to:

identifying a pathological region of the patient based on the delta R1 map generated by the system of claim 17, wherein the pathological region is identified by a difference in values for adjacent voxels.

35. A system for identifying a pathological condition in a patient, wherein the processing circuit is further configured to:

identifying a pathological region of the patient based on the delta R1 map generated by the system of claim 19, wherein the pathological region is identified by a difference in values for adjacent voxels.

* * * * *